United States Patent
Pekander et al.

(10) Patent No.: US 10,517,488 B2
(45) Date of Patent: Dec. 31, 2019

(54) PATIENT MONITORING SYSTEM AND LEADSET HAVING MULTIPLE CAPACITIVE PATIENT CONNECTORS AND A SINGLE GALVANIC PATIENT CONNECTOR

(71) Applicant: General Electric Company, Schenectady, NY (US)

(72) Inventors: Otto Valtteri Pekander, Helsinki (FI); Ville Vartiovaara, Helsinki (FI); Juha Petri Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 477 days.

(21) Appl. No.: 15/387,264

(22) Filed: Dec. 21, 2016

(65) Prior Publication Data

US 2018/0168458 A1    Jun. 21, 2018

(51) Int. Cl.
*A61B 5/0402* (2006.01)
*A61B 5/0205* (2006.01)
(Continued)

(52) U.S. Cl.
CPC ........ *A61B 5/0205* (2013.01); *A61B 5/04284* (2013.01); *A61B 5/0809* (2013.01);
(Continued)

(58) Field of Classification Search
CPC .............. A61B 5/0402; A61B 5/04284; A61B 2562/0214
See application file for complete search history.

(56) References Cited

U.S. PATENT DOCUMENTS

| 5,206,602 A | 4/1993 | Baumgartner et al. |
| 5,307,817 A * | 5/1994 | Guggenbuhl ........ A61B 5/0006 128/908 |

(Continued)

FOREIGN PATENT DOCUMENTS

| EP | 1359842 B1 | 5/2009 |
| EP | 2559280 A1 | 2/2013 |

(Continued)

OTHER PUBLICATIONS

Pending U.S. Appl. No. 14/586,393, filed Dec. 30, 2014, "Common Display Unit for a Plurality of Cableless Medical Sensors", Muuranto.

(Continued)

*Primary Examiner* — Puya Agahi
(74) *Attorney, Agent, or Firm* — Andrus Intellectual Property Law, LLP

(57) ABSTRACT

A patient monitoring system comprises a data acquisition device that records physiological signals from a patient, the data acquisition device having at least 3 receiving ports, each receiving port configured to connect to a patient connector. The monitoring system further includes a galvanic patient connector that galvanically connects a first receiving port of the patient connector and the patient, and at least a first capacitive patient connector and a second capacitive patient connector. Each capacitive patient connector capacitively couples a respective receiving port of the data acquisition device and the patient.

17 Claims, 5 Drawing Sheets

(51) Int. Cl.
*A61B 5/08* (2006.01)
*A61B 5/0428* (2006.01)
*A61B 5/00* (2006.01)

(52) U.S. Cl.
CPC ........... *A61B 5/0402* (2013.01); *A61B 5/7217* (2013.01); *A61B 5/7225* (2013.01); *A61B 2562/0214* (2013.01)

(56) References Cited

U.S. PATENT DOCUMENTS

| | | | |
|---|---|---|---|
| 6,377,845 B1 | 4/2002 | Kinast | |
| 6,496,705 B1 | 12/2002 | Ng et al. | |
| 6,749,566 B2 | 6/2004 | Russ | |
| 7,390,299 B2 | 6/2008 | Weiner et al. | |
| 8,475,368 B2 | 7/2013 | Tran et al. | |
| 8,630,699 B2 * | 1/2014 | Baker | A61B 5/0006 600/509 |
| 2004/0173003 A1 | 9/2004 | Ibane | |
| 2006/0136768 A1 | 6/2006 | Liu et al. | |
| 2006/0284621 A1 | 12/2006 | Doi | |
| 2007/0135701 A1* | 6/2007 | Fridman | A61B 5/0408 600/382 |
| 2008/0284599 A1 | 11/2008 | Zdeblick | |
| 2009/0318818 A1 | 12/2009 | Whitaker et al. | |
| 2010/0168605 A1 | 7/2010 | Aarts | |
| 2011/0004090 A1* | 1/2011 | Keightley | A61B 5/0408 600/383 |
| 2011/0066051 A1 | 3/2011 | Moon | |
| 2011/0145894 A1 | 6/2011 | Morchon et al. | |
| 2012/0068855 A1 | 3/2012 | Matsumura | |
| 2012/0108917 A1 | 5/2012 | Libbus et al. | |
| 2013/0053674 A1 | 2/2013 | Volker | |
| 2013/0109927 A1 | 5/2013 | Menzel | |
| 2013/0289376 A1 | 10/2013 | Lang | |
| 2013/0337842 A1 | 12/2013 | Wang et al. | |
| 2014/0187883 A1 | 7/2014 | Lisogurski | |
| 2015/0116130 A1 | 4/2015 | Grubis | |
| 2015/0190066 A1* | 7/2015 | Boege | A61B 5/0404 600/509 |
| 2016/0183836 A1* | 6/2016 | Muuranto | A61B 5/04288 600/301 |
| 2017/0251939 A1* | 9/2017 | Santala | A61B 5/0402 |

FOREIGN PATENT DOCUMENTS

| | | |
|---|---|---|
| EP | 1881784 B1 | 10/2013 |
| WO | 2014027273 A1 | 2/2014 |

OTHER PUBLICATIONS

Radius-7 brochure, MASIMO, admitted prior art.
IntelliVue Cableless Measurement brochure, Philips, Jun. 2013.
http://electronicdesign.com/power/lightning-bolts-defibrillators-and-protection-circuitry-save-lives.
Soundarapandian et al., "Analog Front-End Design for ECG Systems Using Delta-Sigma ADCs", Texas Instruments, SBAA160A, Mar. 2009, Revised Apr. 2010.
Torres, Bernat Albet., "Wireless System for the Measurement of Bioelectric Signals using Capacitive Electrodes", Universitat Politecnica de Catalunya.
International Search Report and Written Opinion for International Application No. PCT/US2017/066401 dated Feb. 23, 2018. 10 pages.

* cited by examiner

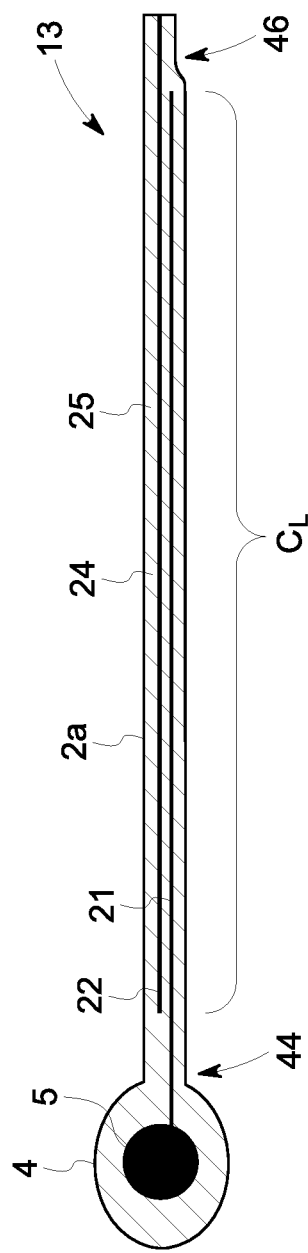
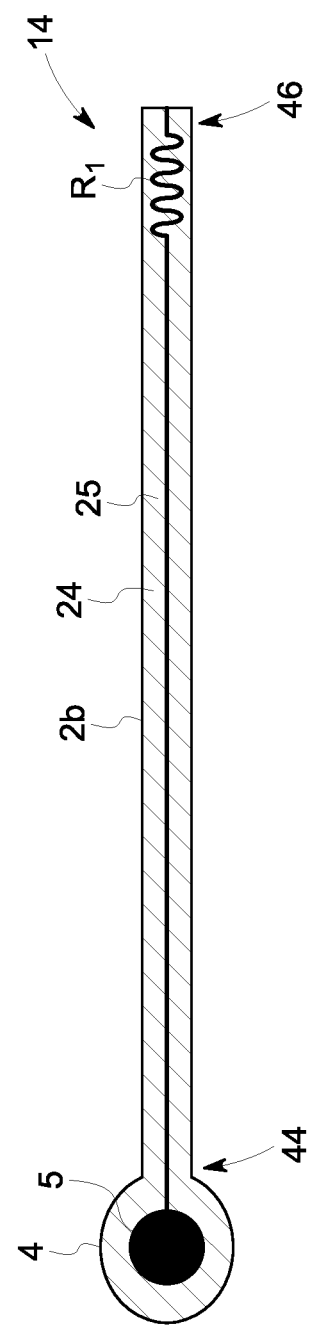
FIG. 5A
FIG. 5B

PATIENT MONITORING SYSTEM AND LEADSET HAVING MULTIPLE CAPACITIVE PATIENT CONNECTORS AND A SINGLE GALVANIC PATIENT CONNECTOR

BACKGROUND

This disclosure generally relates to medical monitoring systems and devices, and more specifically to leadwires for ECG and/or respiratory monitoring.

Electrocardiograms (ECGs) are graphic depictions of electrical activity in the heart, i.e. cardiac potentials. ECGs are produced by electrocardiographs which are available as stand alone devices, portable devices, and/or as integrated functions in various types of multi-vital sign monitoring devices. ECGs are depicted by time (ms) versus voltage (mV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient.

Respiration monitors are also available that use chest electrodes that are similar or identical to ECG electrodes. For example, respiration rate measurement may be determined using impedance pneumography, where a high-frequency A/C current is passed between at least two electrodes (often the right arm electrode and left arm electrode), including a driving electrode and a receiving electrode, on the patient's chest and an impedance between the electrodes is determined. Respiration is then monitored according to the changing impedance values as the patient breathes. As the patient inhales, air (which is an insulator) enters the lungs and causes the net impedance in the circuit to increase. When the patient exhales, air leaves the lungs and causes the impedance in the circuit to decrease.

Both electrocardiographs and respiration monitors (which may be separate devices or contained in a single device using a common set of electrodes) must have protection circuitry to protect the electronics of those devices from high voltage exposure due to operation of a defibrillator on a patient to which the monitoring devices are connected. Patients experiencing sudden cardiac arrest are treated with a defibrillation shock to the chest. The defibrillation shock is typically in the range of 3 to 5 kilovolts and 50 amps, and typically lasts between 5 and 20 milliseconds. Such a high voltage and current are necessary in order to stop the patient's heart from unproductive fluttering (fibrillating) and to allow the heart to restart effective pumping of blood. Typically, respiration monitors and electrocardiographs are separate from the defibrillator device, and the chest electrodes and leadwires are connected to the patient when the defibrillator delivers the shock. Thus, the electrocardiograph and respiration monitors must withstand the significant voltage and current of the defibrillation and continue working properly.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a patient monitoring system comprises a data acquisition device that records physiological signals from a patient, the data acquisition device having at least 3 receiving ports, each receiving port configured to connect to a patient connector. The monitoring system further includes a galvanic patient connector that galvanically connects a first receiving port of the patient connector and the patient, and at least a first capacitive patient connector and a second capacitive patient connector. Each capacitive patient connector capacitively couples a respective receiving port of the data acquisition device and the patient.

A respiration monitoring system comprises a data acquisition device that records cardiac potentials from a patient, the patient monitoring having at least three receiving ports that are each configured to connect to a patient connector. The system further includes a galvanic patient connector that galvanically connects a first receiving port of the data acquisition device and the patient, and at least a first capacitive patient connector and a second capacitive patient connector. Each capacitive patient connector capacitively couples a respective receiving port of the data acquisition device and the patient. The cardiac potentials are recorded from the patient between the first capacitive patient connector and the second capacitive patient connector, and the galvanic patient connector acts as a reference.

One embodiment of a lead set for recording physiological signals from a patient includes a galvanic patient connector comprising a conductive leadwire and a galvanic electrode, and two or more capacitive patient connectors. Each capacitive patient connector includes a capacitive leadwire connecting to a galvanic electrode. The capacitive leadwire includes an electrode end connecting to the galvanic electrode, a first conductive layer extending from the electrode end, a device end connectable to a data acquisition device, and a second conductive layer extending from the device end toward the electrode end. Wherein the capacitive leadwire is configured such that the first conductive layer is galvanically isolated from the second conductive layer such that the first conductive layer and the second conductive layer form a capacitor.

Various other features, objects, and advantages of the invention will be made apparent from the following description taken together with the drawings.

BRIEF DESCRIPTION OF THE DRAWINGS

The present disclosure is described with reference to the following Figures.

FIG. 5A depicts one embodiment of a capacitive patient connector.

FIG. 5B depicts one embodiment of a galvanic patient connector.

DETAILED DESCRIPTION

Figure 1:
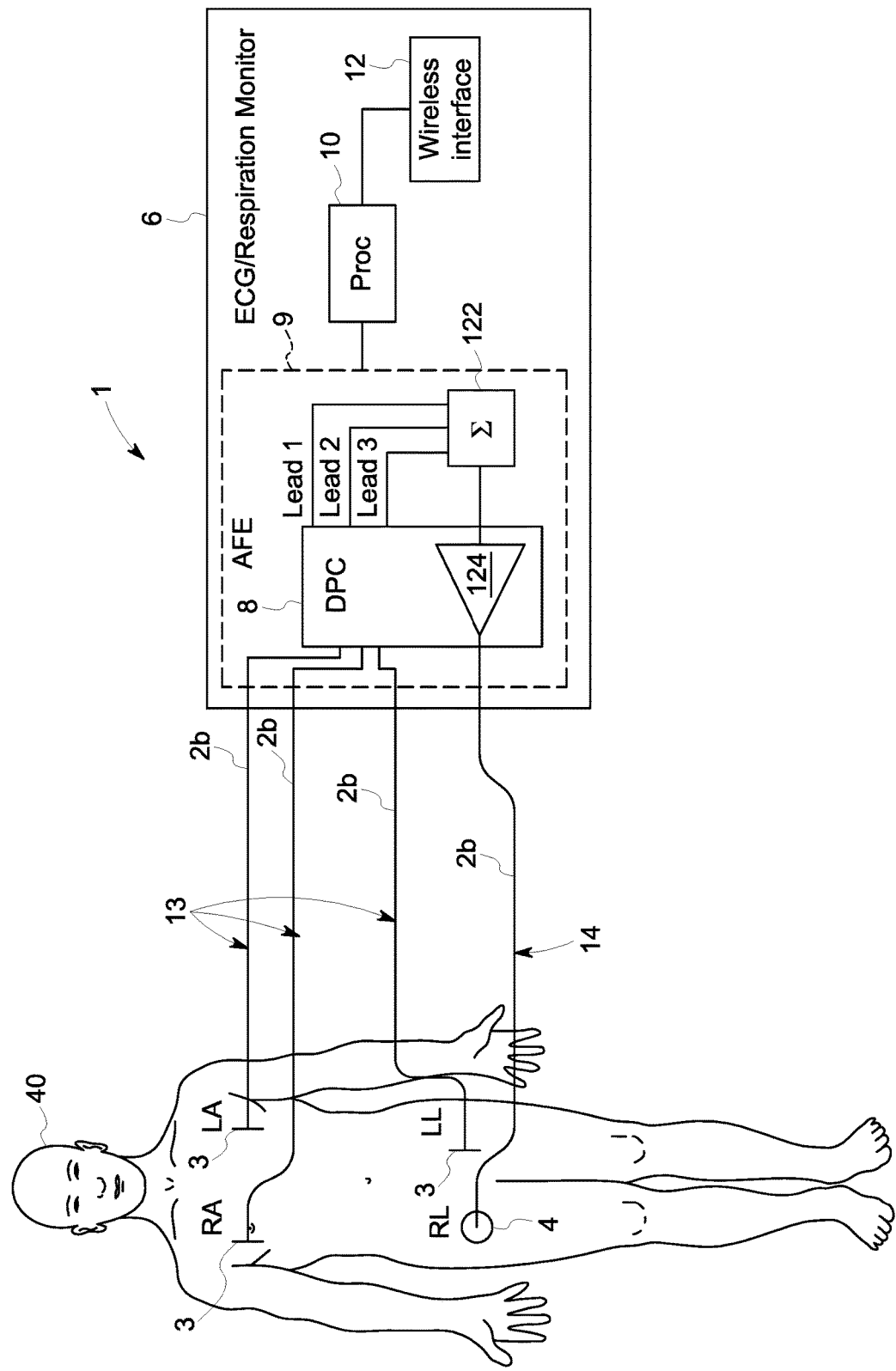
FIG. 1 depicts one embodiment of a patient monitoring system having a single galvanic patient connector and multiple capacitive patient connectors for recording physiological signals from a patient.

As described above, electrocardiographs and respiration monitors must be configured to withstand the high voltage defibrillation pulses, which are on the order of 3 to 5 kilovolts and 50 amps and last for 5 to 20 milliseconds (which is a long time for electronic components to survive such high voltage). Thus, such monitoring devices are typically provided with defibrillation protection circuitry at their inputs which is designed to absorb the energy of the high voltage pulse before it reaches the sensitive electronics. Defibrillation protection in electrocardiograph and respiration monitoring devices has traditionally been implemented with resistors, which are large and expensive because they must be designed to cope with huge defibrillation power surges. Additionally, resistive components introduce thermal noise. For example, the energy travelling through an average 10 kiloohm resistor from a 5 kilovolt defibrillation pulse can cause the resistor to reach very high temperatures, such as internal temperatures reaching 200° Celsius or higher. This significant heating of the resistor causes it to break down.

The present inventors have recognized that the use of capacitive, or more generally reactive, impedance in place of or in addition to such passive resistive components enables the use of high impedance levels without inherent noise issues. Accordingly, the present inventor is has recognized that capacitive patient connectors, such as capacitive electrodes or capacitive leadwires, can be utilized to protect against the defibrillation pulse. Additionally, the present inventors have recognized that the leadwires, which connect chest electrodes on the patient to data acquisition devices of patient monitors, can be created so that the length of the leadwire provides capacitive transmission of physiological signals recorded at the electrode. This allows for inclusion of a relatively large capacitive element providing significant protection against the defibrillation pulse without increasing the overall size of the leadwire or the data acquisition device.

In addition to the electrically isolating properties of capacitive patient connectors, the inventor has recognized that the use of capacitive electrodes has the added benefit of avoiding conductive gels and pastes, such as silver/silver chloride gel, which are used in typical chest electrodes and are often irritating to the skin. Such irritation can be especially problematic if the electrodes are to be worn by the patient over a long period of time, or if the patient has particular sensitivity or allergy to the conductive pastes and gels utilized in conductive surface electrodes.

Capacitive patient connectors solve the aforementioned defibrillation resistor problems; however, the inventors have recognized that capacitive sensor topologies generally suffer from issues due to unreliability and low quality, especially for the purpose of diagnostic ECG. For example, capacitive sensor topologies often have wandering and suddenly changing DC offset. This can cause challenges when trying to keep all of the recorded physiological signals in the correct DC offset range for the analog front end (AFE). Another problem with capacitive topologies recognized by the inventors is that capacitive sensors do not provide good coupling to the patient for the purposes of measuring changes in impedance due to respiration.

In view of the recognition of the foregoing problems with capacitive technologies and their recognition of the benefits of capacitively coupling the patient to the data acquisition device, the inventors developed the solution disclosed herein where one single patient connector in the lead set is resistive providing a DC path for ECG monitoring and good coupling for impedance respiration, while the remainder of the patient connectors and the lead set are capacitive. Therefore, there is no current path with low resistance for the defibrillator pulse to travel, but the DC offsets can still be managed.

Accordingly, in the system developed by the inventors, the data acquisition device connects to one galvanic patient connector that galvanically connects the data acquisition device to the patient, and two or more capacitive patient connectors used to measure physiological potentials from the patient, wherein each capacitive patient connector capacitively couples the data acquisition device to the patient. The capacitive patient connector may include a capacitive electrode that capacitively couples to a patient's skin, or could include a capacitive lead wire, which is described herein. In still another embodiment, a capacitor may be provided at the receiving port of the data acquisition device 6, such as the initial element of the defibrillation protection circuit 8 in the analog front end 9.

FIG. 1 depicts one embodiment of a patient monitoring system 1 having three capacitive patient connectors 13 and a galvanic patient connector 14 connecting the data acquisition device 6, which is a combined respiration monitor and ECG monitor, to the patient 40. Specifically, the capacitive patient connectors 13 comprise capacitive electrodes 3 coupled to the patient's chest with conductive leadwires 2b connecting a capacitive electrode 3 to the data acquisition device 6. The capacitive patient electrodes 3 are in the right arm position RA, the left arm position LA, and the left leg position LL. The depicted electrode arrangement is for purposes of explanation, and a person having ordinary skill in the art will understand in light of the present disclosure that any number of capacitive patient connectors 13 may be included and received by the data acquisition device 6. For example, in 12 lead ECG applications ten electrodes may be used and connected to the data acquisition device 6. In such embodiments, the defibrillation protection circuit 8 in the analog front end 9 includes protection circuit elements for each input. The patient connectors 13, 14 may be disposable elements or reusable elements, and in a preferred embodiment removably connect to the data acquisition device 6, such as at a receptacle 37 in a housing of the data acquisition device 6.

The capacitive electrode 3 may be any capacitive electrode that uses capacitance for bioelectric measurement. A person having ordinary skill in the art will know that several different capacitive electrodes already exist in the market. For example, the capacitive electrode may be the QUASAR IBE by Quantum Applied Science and Research, Inc. of San Diego, Calif. As described above, the capacitive electrode 3 may be fixed directly to the patient's skin, and thus may touch the patient's skin, or may be separated from the patient's skin by a material, such as a garment or a band to which the capacitive electrode may be fixed.

The data acquisition device 6 may be any type of physiological monitoring device involving electrodes to the patient, especially those involving chest electrodes where defibrillation protection is required. For example, the data acquisition device 6 may be an ECG monitor that records cardiac potentials from the patient or a respiratory monitor, such as an impedance pneumograph, that records physiological potentials relevant to respiratory monitoring. The data acquisition device 6 serves to collect the physiological data recorded from the patient 40 and store or transmit the physiological data to a hub device, central data acquisition device, or host network for the medical facility. In the depicted embodiment, the data acquisition device 6 has a processor 10 that receives digitized physiological data from the analog front end 9, and controls a wireless interface 12 to transmit the physiological data for further processing and/or storage in a patient's medical record.

As discussed above, capacitively coupling the patient 40 to the data acquisition device 6 via capacitive patient connectors leads to performance issues due to DC drift. For example, the static potential of the patient's body will change as the patient moves, and such changes can happen quite quickly. This changing DC potential can saturate the amplifiers, which temporarily inhibits reliable patient monitoring. In normal patient monitoring using galvanic electrodes, such as standard ECG monitoring, the body potential is typically set to a certain DC potential, or offset voltage. However, that control of the DC potential does not occur in a purely capacitive coupling situation.

Accordingly, the present inventors developed the depicted embodiment where one, and only one, galvanic patient connector 14 is provided that serves as a single DC reference electrode that galvanically connects to the patient, thus serving as a reference electrode to remove DC drift, and thus improve performance of the data acquisition device by eliminating the noise and amplifier saturation issues. Further, the single galvanic patient connector 14 allows respiration measurement by serving as a ground when the high frequency current is driven through the capacitive patient connectors 13 for the purpose of monitoring respiration potentials.

FIG. 1 provides a schematic diagram of one possible configuration for utilizing the galvanic patient connector 14 as a reference electrode. Each of the three lead channels are added by the summing circuit 122 to create a patient common mode voltage. In various embodiments, the galvanic patient connector 14 may simply provide a passive low-resistance path to ground, or it may be connected to an active circuit in the data acquisition device 6 (such as in the AFE), often referred to as a "right leg driver." In such an embodiment, as depicted, the common mode voltage output of the summing circuitry 122 drives an inverting amplifier 124, which in turn drives the galvanic patient connector 14. In the depicted embodiment, the galvanic patient connector 14 includes a galvanic electrode 4 connected to the patient 40 at the right leg position RL. Thereby, the galvanic electrode 4 in the right leg position RL acts to subtract the common mode noise, including providing DC offset subtraction.

In other embodiments, the galvanic patient connector 14 may provide a passive path to ground. For example, the system 1 in FIG. 1 may provide impedance respiration monitoring, such as by monitoring the change in resistance to a drive current between the capacitive electrode 3 in the right arm position RA and in the left leg position LL, where the galvanic patient connector 14 provides a ground for that drive current delivered by the capacitive electrodes 3. As described above, the drive current has a carrier frequency that corresponds with the value.

Figure 2:
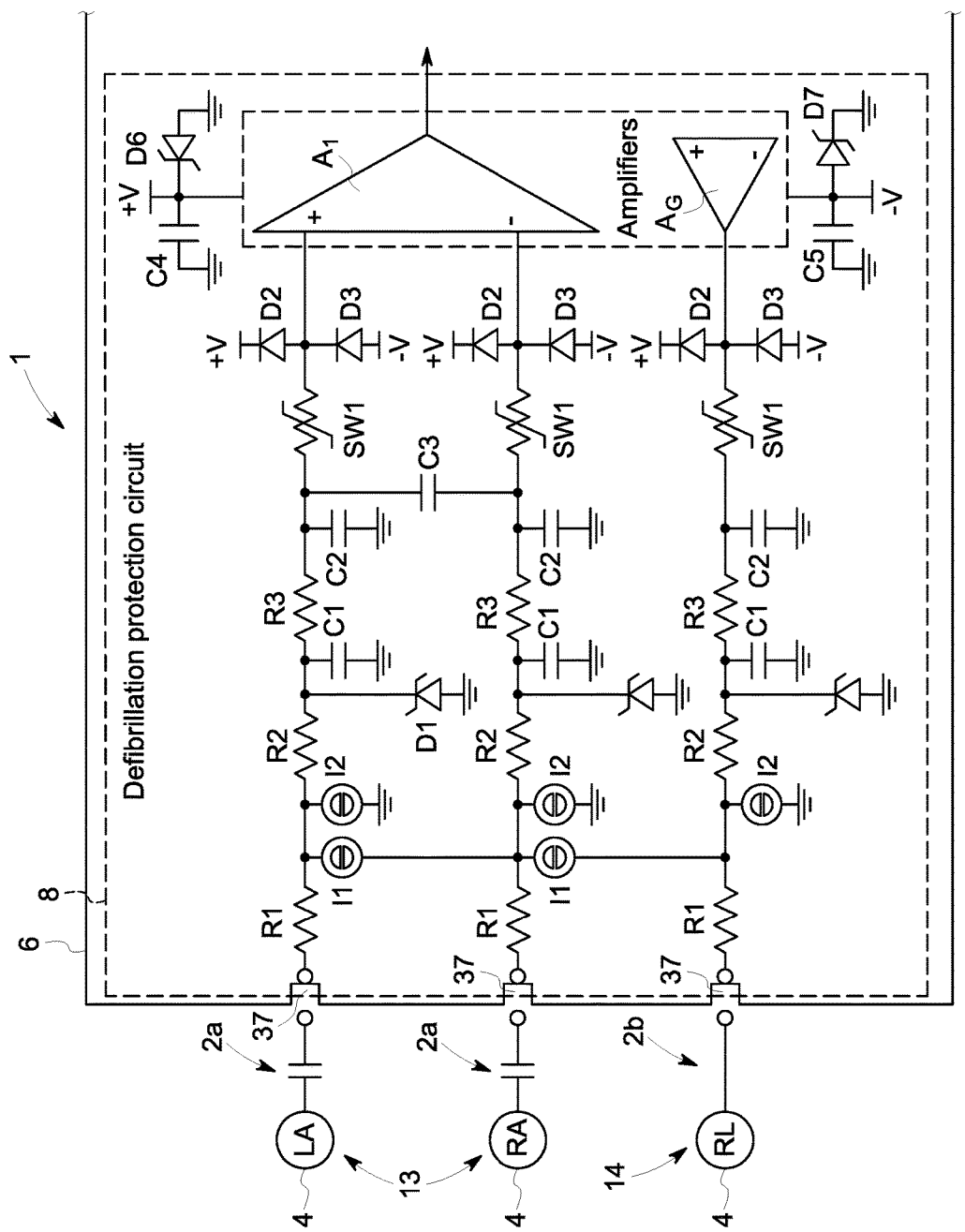
FIG. 2 depicts another embodiment of a patient monitoring system including a data acquisition device with a defibrillation protection circuit and a leadset having a single galvanic patient connector and multiple capacitive patient connectors for recording physiological signals from a patient.

FIG. 2 depicts another embodiment where the capacitive patient connectors 13 comprise capacitive lead wires 2a, rather than capacitive electrodes 3. The capacitive patient connector 13 includes a galvanic electrode 4, such as a standard chest electrode adhering to the patient with silver/silver chloride gel, and a capacitive leadwire that capacitively couples the galvanic electrode 4 (which is attached to the patient) and a receptacle 37 of the data acquisition device 6.

FIGS. 4A-4D depict various embodiments of the capacitive leadwire 2. In general, the capacitive leadwire 2 has a first conductive layer 21 and a second conductive layer 22 that are galvanically isolated and form a capacitor along the length of the capacitive leadwire 2a. For example, the first conductive layer 21 and the second conductive layer 22 may be parallel wires divided by a substrate 24, which is an insulator having known dielectric properties. The first conductive layer 21 extends from the electrode end 44 of the capacitive leadwire 2a, and is in galvanic contact with a conductive portion 5 of the chest electrode 4. The first conductive layer 21 extends along at least a portion of the length of the capacitive leadwire 2a, and in many embodiments extends for a majority of the length of the capacitive leadwire 2a. The second conductive layer extends from the device end 46 of the capacitive leadwire 2a. The second conductive layer 22 also extends at least a portion of the length of the capacitive leadwire 2a so that its length sufficiently intersects the length of the first conductive layer 21 so that the two layers can form a capacitor $C_L$.

As depicted in FIG. 5A, for example, the cross over area between the first conductive layer 21 and the second conductive layer 22 form a capacitor $C_L$ that may span a majority of the length of the capacitive leadwire 2a. In other embodiments, the capacitive area $C_L$ may be larger or smaller compared to the total length of the leadwire 2a. In the embodiments depicted and described, the capacitance of the capacitive aspect $C_L$ of the leadwire 2a can be adjusted and controlled by adjusting the area of overlap between the conductive layers 21 and 22 and adjusting the separation between the conductive layers 21 and 22. Furthermore, the capacitance is also affected by the permittivity of the material comprising the substrate 24 between the conductive layers 21 and 22.

FIG. 2 depicts a circuit diagram of an exemplary defibrillation protection circuit 8 provided at the input of a data acquisition device 6 for acquiring cardiac or respiration signals from a patient, and capacitive leadwires 2 that are connectable to the defibrillation protection circuit. The capacitive leadwires 2 connect chest electrodes 4 to the data acquisition device, where the defibrillation protection circuit 8 resides as a front end protection circuit. In the example, three chest electrodes 4 are depicted for purposes of explanation, which include the left arm electrode LA, right arm electrode RA, and right leg electrode RL. As will be understood by a person having ordinary skill in the art in light of this disclosure, any number of electrodes may be included and received by the data acquisition device 6. For example, in 12-lead ECG applications ten or more electrodes may be used and connected to the data acquisition device 6. In such embodiments, the defibrillation protection circuit 8 includes protection circuit elements for each input. The leadwires 2 may be disposable elements or reusable elements, and in a preferred embodiment removably connect to the data acquisition device 6, such as at a receptacle 37 in a housing of the data acquisition device 6.

In the depicted example, the defibrillation protection circuit 8 provided at the front end of the data acquisition device 6 includes a resistor $R_1$ at the galvanic connection point of each receptacle 37. For example, the resister $R_1$ may be in the range of 10 to 20 kiloohms, or even as high as 100 kiloohms. For each input, the resistor $R_1$ may be connected in series with one or more voltage absorption elements $I_1$ and $I_2$, which are configured to absorb at least a portion of the energy exiting the resistor $R_1$ during a defibrillation event. For example, $I_1$ and $I_2$ may be neon glow lamps, where a small radioactive dot inside a gas tube provides photons to stabilize the ionization voltage. Such neon glow lamps are commonly used in defibrillation protection circuits 8. Alternatively, $I_1$ and $I_2$ may be gas-discharge arrestor tubes or transient voltage suppressors, which are also known to be used for such purposes.

Resistors $R_2$ and $R_3$, along with capacitors $C_1$, $C_2$, and $C_3$ form low pass filters for each input. The diode $D_1$ limits the voltage to a lower level. For example, diode $D_1$ may be a Zener diode or an Avalanche diode, a metal oxide varistor, or a thyristor surge protector. The diode $D_1$ in conjunction with the capacitor $C_1$ provide the first part of a low pass filter. Capacitor $C_2$ acts as a common-mode filter, and capacitor $C_3$ provides differential filtering. Typically, capacitor $C_3$ is about ten times larger than capacitor $C_2$. A high-voltage signal-line protector $SW_1$ follows the low pass filter and is a switch that senses high voltage and turns on a clamp to reduce the amount of voltage permitted to reach the respective amplifier. In alternative embodiments, the current limiting element may instead be a current-limiting diode. Diodes $D_2$ and $D_3$ are electrostatic discharge protection diodes that clamp the amplifier input to the power supplies. Capacitor $C_4$ and Zener diode $D_6$ are connected to the amplifiers to absorb and clamp the positive voltage rail. Capacitor $C_5$ and Zener diode $D_7$ are also connected to the amplifiers in order to absorb and clamp the negative voltage rail.

The embodiment of FIG. 2 is depicted as including galvanic electrodes 4 at the left arm position LA and right arm position RA, and a galvanic patient connector having a galvanic electrode 4 at the right leg position RL. The amplifier $A_1$ puts an output potential based on the left arm and right arm inputs. As described above, in an embodiment comprising an active circuit that drives the reference lead, which in the depicted embodiment is the right leg electrode RL, the output of $A_1$ is summed with other output potentials from other leads and provided to the amplifier $A_G$, which as described above is an inverting amplifier that drives the right leg electrode RL. It should be noted that, while the depicted embodiments show the galvanic electrode 4 of the galvanic patient connector 14 connected at the right leg position RL, the galvanic patient connector may connect at any other location on the patient 40.

The defibrillation protection circuit 8 may be incorporated in or followed by an analog front end 9 (AFE) which filters and digitizes the analog signals that emerge from the defibrillation protection circuit 8. Various analog front end designs are well known. In certain embodiments, the defibrillation protection circuit 8 and the analog front end 9 may be integrated into a single device or arrangement.

The inventors of the present application have recognized that such defibrillator protection circuits may be insufficient for providing protection from defibrillation pulses, especially as data acquisition devices 6 become smaller and it is desired to reduce the size of the components and the overall circuit. Accordingly, the inventors have endeavored to provide a more robust defibrillation protection system that reliably incorporates capacitive patient connectors in order to isolate the data acquisition device 6 from defibrillation pulses. For example, in the context of wireless patient monitoring, it is desirable to provide a data acquisition device 6 that can be worn by or attached to the body of a patient. In such an embodiment, it is desirable to provide a small and light data acquisition device 6 that can wirelessly transmit physiological data gathered from the patient, such as ECG data or respiration data, to a hub device or host computer network associated with the patient physiological monitoring system.

Figure 3:
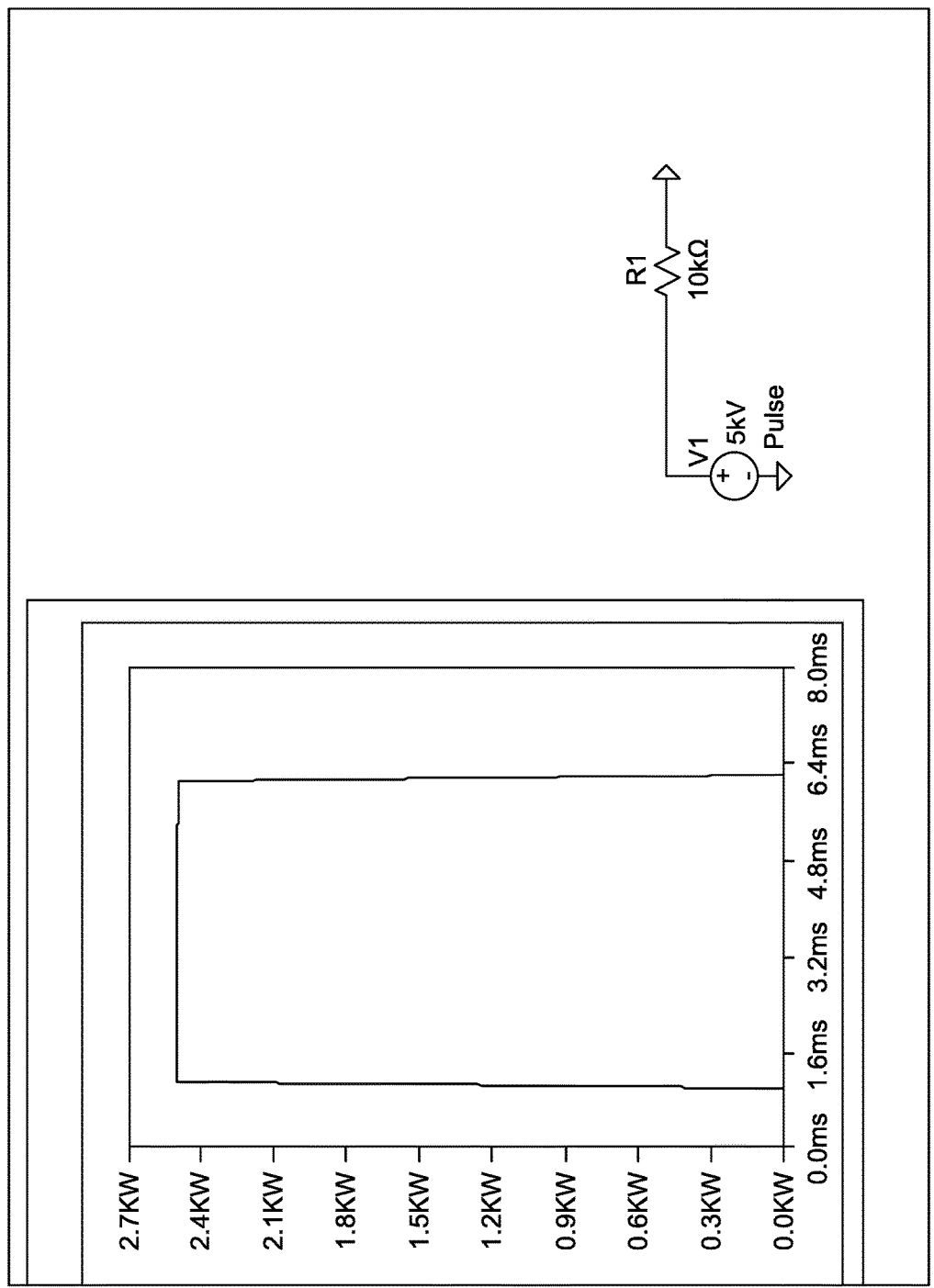
FIG. 3 is a graph depicting power measured at the output of a first resistor typically provided at the front end of a defibrillation protection circuit.
Figure 4:
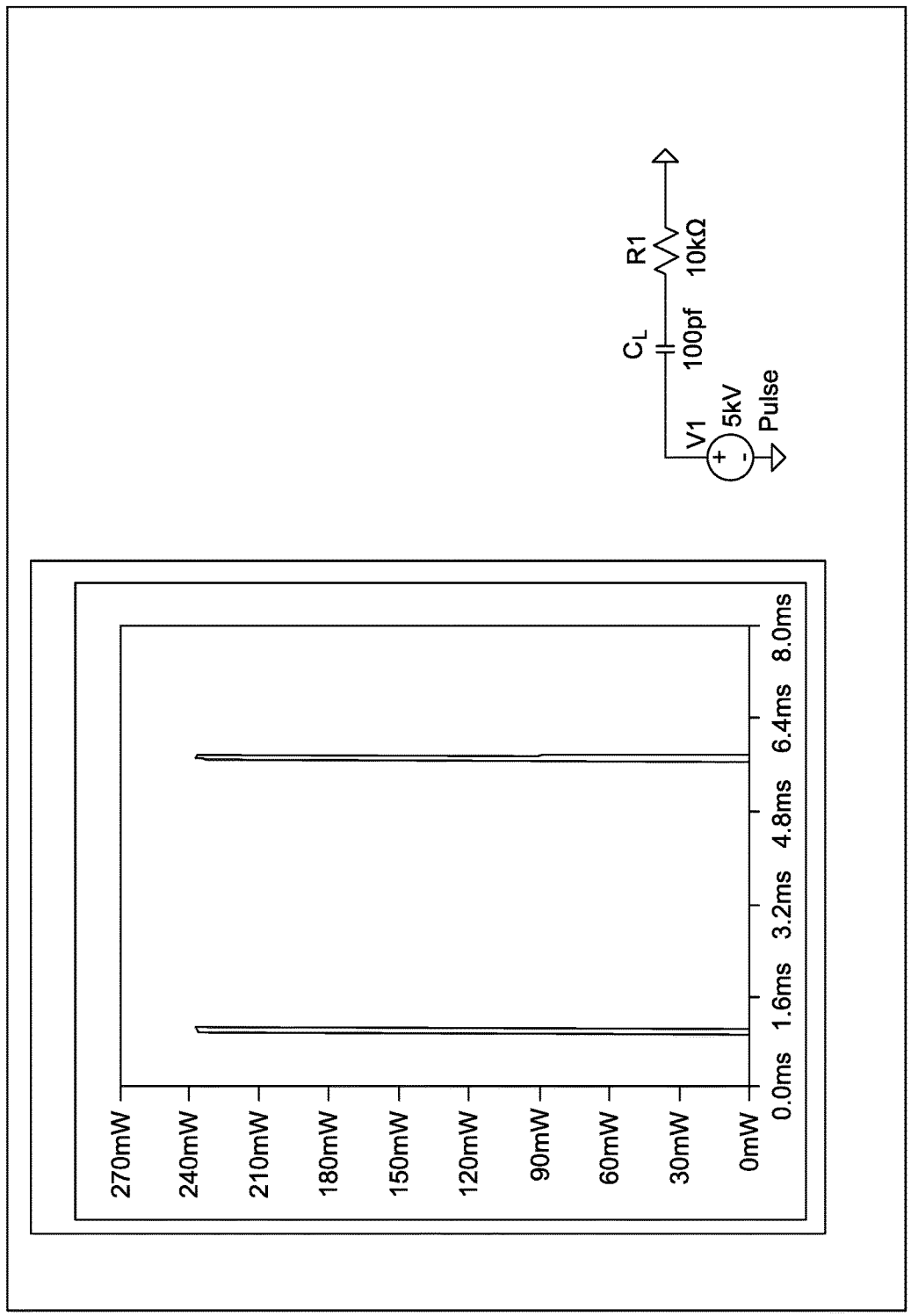
FIG. 4 is a graph depicting the power at the output of the first resistor of the defibrillation protection circuit when a capacitive leadwire of the present disclosure is utilized.

Comparison between the graphs of FIGS. 3 and 4 exemplifies the benefit of using the capacitive patient connectors 13 described herein. FIG. 3 depicts the power transferred through the 10 kiloohm resistor $R_1$, which is a typical resistor provided at the input of a defibrillation protection circuit 8, during a 5 kilovolt pulse, which represents a typical defibrillation pulse that might be administered to a patient experiencing cardiac arrest. As can be seen, the resistor $R_1$ encounters about 2.5 kilowatts of power instantaneously at the start of the defibrillation pulse and experiences that power for the duration of the pulse. In the depicted embodiment where the pulse has a duration of approximately 5 milliseconds, the energy transferred through the resistor $R_1$ approaches 13 joules, which is a very large amount of energy in a very short period of time.

This can be compared to the graph in FIG. 4, where the same 5 kilovolt, 5 millisecond pulse is input to a system having a capacitive leadwire 2a connecting between the electrode absorbing the pulse from the patient's chest and the data acquisition device 6. In the depicted embodiment, the capacitor $C_L$ formed by the capacitive leadwire 2a has a 100 picofarad capacitance. As demonstrated in the graph, the power measured at the output of the resistor $R_1$ is minimal compared to the configuration without the capacitive leadwire $C_L$, where the power through resistor $R_1$ peaks at about 250 milliwatts at the beginning and end of the defibrillation pulse, and the total energy through the resistor $R_1$ is only about 50 microjoules. Thus, the resistor $R_1$ will not experience heating, and the size of the resistor can even be decreased if desired. The depicted test pulse has a 0.1 millisecond rise and fall time, meaning that the capacitor $C_L$ has time to adjust. However, even if the rise time is much shorter, such as 1 microsecond, the total energy still remains below 2 millijoules, which is still a significant decrease from the 13 joules of energy without the capacitive leadwire 2.

When using the capacitive leadwire 2, the capacitive value of capacitor $C_L$ may be adjusted to ensure that the target frequencies are transmitted and are not filtered out. For example, when utilizing the capacitive leadwire 2 for monitoring respiration, one needs to utilize a high enough carrier frequency that will not be filtered out by the capacitor. For instance, if the carrier frequency is 50 kilohertz (which is common in respiration monitoring), one would use 1nanofarads capacitor $C_L$. In certain applications, it may be desirable to utilize a higher carrier frequency, such as 1 megahertz, and decrease value of the capacitor $C_L$ to 100 picofarads.

In certain embodiments, the capacitive leadwire 2a and/or the conductive leadwire 2b may be formed by printing the conductive layers 21 and 22 on a substrate 24. For example, the conductive layers 21 and 22 may be conductive traces printed on the substrate 24 with conductive ink. Conductive ink is a liquid ink dispensable by a specialized printer to form an object that conducts electricity. The transformation from liquid ink to a solid conductor may involve a drying or curing process. Such inks allow circuits to be drawn or printed on a variety of substrate material, and typically contain conductive materials such as powdered or flaked silver and carbon-like materials, although polymeric conduction is also known. As will be understood by a person having ordinary skill in the art in view of this disclosure, a number of conductive inks are available and appropriate for printing a conductive trace onto a flexible substrate 24 to provide a continuous conductor of a predefined length. The conductive portion 5 of the galvanic electrode 4 may also be printed, such as on the substrate material 24.

The flexible substrate 24 may be comprised of any number of materials. In one embodiment, the flexible substrate 24 is a thermal plastic polyurethane (TPU). Alternatively, the flexible substrate 24 may be a polyethylene terephthalate (PET), or any other plastic material sufficiently flexible to be used as a substrate for purposes of providing a leadwire connecting between an electrode and a data acquisition device 6.

FIG. 5A depicts one embodiment of a printed capacitive patient connector 13, and FIG. 5B depicts one embodiment of a printed galvanic patient connector 14. In FIG. 5A, the first conductive layer 21 and the second conductive layer 22 are printed on a first side 25 of a substrate 24. The conductive layers 21 and 22 are parallel printed traces, with the first conductive layer 21 extending from the electrode end 44 and the second conductive layer 22 extending from the device end 46 of the capacitive leadwire 2a. As described above, the first conductive trace 21 may extend to a conductive portion 5 of an electrode 4, which may also be a printed element.

The first conductive layer 21 is printed on a first side 25 of the strip of substrate 24, which is for example a long and thin strip of TPU. The first conductive layer is, for example, a first trace printed on the bottom side 25 starting at the electrode end 44 of the leadwire 2 and continuing most of the length of the leadwire 2, as is depicted. A second conductive layer 22 is also printed on the first side 25 of the strip of substrate 24. The second conductive layer extends from the device end 46 of the leadwire 2 across most of the length of the leadwire. Accordingly, the first conductive layer 21 and the second conductive layer 22 are separated by the substrate material 24, and thus are galvanically isolated. The mutual capacitance between the two adjacent parallel conductive layers 21 and 22 transmits the physiological signals recorded from the patient during normal monitoring operation. However, upon delivery of a defibrillation pulse, the capacitor $C_L$ saturates in the voltage across the capacitor $C_L$ is effectively zero. This is demonstrated in FIG. 3, where the capacitor $C_L$ blocks transmission of the of the high voltage defibrillation pulse.

The electrode end 44 in the embodiment of FIGS. 5A and 5B could be provided with an element to connect to an electrode, or an electrode could be formed or attached by any means. Alternatively, the electrode may be provided with attachment means, such as a clip capable of puncturing any insulation layer and making galvanic connection to the first conductive layer 21.

The geometry of the conductive layer 21, 22 and their arrangement may be varied, whether in a printed embodiment or in a leadwire 2a, 2b constructed by other means. For example, the conductive layers 21, 22 may be plate-like, being relatively narrow (such as a width of 1-3 centimeters) and long (such as 1-3 feet) extending the length of the leadwire 2. In another embodiment, the second conductive layer 22 is printed on a second side of the strip of substrate 24, such as on the top, or opposite, side as the first conductive layer 21. In still other embodiments, the first conductive layer 21 and the second conductive layer 22 may be arranged in a coaxial configuration where one of the conductive layers 21, 22 forms a cylinder surrounding the other conductive layer 21, 22, which is a cylindrical wire, with the substrate material 24 dividing the two layers.

A printed galvanic patient connector 14 similarly includes a conductive layer printed on a first side 25 of the strip of substrate 24. As described above, the depicted embodiments provide a printed galvanic electrode 4 having a conductive portion 5 that galvanically connects to the patient 40, such as by the use of silver/silver chloride gel. The conductive portion 5 is also printed. Other elements may also be printed along the length of the leadwire 2b, such as resistive traces or other circuit elements. For example, resistor $R_1$ may be built into the leadwire 2b rather than being incorporated into the defibrillation protection circuit 8 provided in the data acquisition device 6. For example, resistor $R_1$ may be a printed element printed on a top side 26 of the substrate 24. In the embodiment of FIG. 4B, the resistor is printed near the device end 46 of the leadwire 2 and is contained within the device connector 35, which is an element configured to be received by and attached to the receptacle 37 of the data acquisition device 6. In other embodiments, the resistor $R_1$ may be printed on a portion of the leadwire 2 that is outside of the device connector 35, and may be anywhere between the capacitor portion $C_L$ of the leadwire 2 and the device end 46. In still other embodiments, the resistor printed on the second conductive layer 22 may be in addition to the resistor $R_1$ of the defibrillation protection circuit 8, and thus may be in series therewith.

Additionally, an insulating layer may be provided over the conductive layers in order to shield them from noise induced by other magnetic fields, which are common in hospital and healthcare environments. The insulating layer may be printed over the conductive layers 21, 22, or applied over the conductive layers 21, 22 by other means. For example, the insulating layer may be a separate piece of material adhered to the first side 25 of the substrate 24. For instance, the insulating layer may be comprised of the same material as the flexible substrate 24, such as TPU or PET, or may be any other material that sufficiently insulates the conductive layers 21, 22 from noise. For instance, the printed insulating layer may be comprised of ElectrodagPF-455B UV-Curable Insulator Paste by Henkel Corporation or may be 125-17M Screen-Printable UV-Curable Coating by Creative Materials, Inc.

In other embodiments, the electrode end 44 of the respective leadwire 2a, 2b may be provided with an electrode connector configured to connect to any galvanic electrode 4. For example, the electrode connector may be a snap connector configured to connect with a snap electrode. In other embodiments, the electrode connector may be any element capable of galvanically connecting to the electrode 4, such as an alligator clip or clamp.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A patient monitoring system having defibrillation protection, the patient monitoring system comprising:
   a data acquisition device that records physiological signals from a patient, the data acquisition device having at least three receiving ports, each receiving port configured to connect to a patient connector;

a galvanic patient connector that galvanically connects a first receiving port of the data acquisition device and the patient; and at least a first capacitive patient connector and a second capacitive patient connector, wherein each capacitive patient connector capacitively couples a respective receiving port of the data acquisition device and the patient;

wherein the physiological signals include cardiac potentials recorded between the first capacitive patient connector and the second capacitive patient connector; and wherein the galvanic patient connector acts as a reference electrode to remove a DC offset in the cardiac potentials.

2. The patient monitoring system of claim 1, further comprising at least a third capacitive patient connector;

wherein the first capacitive patient connector is connected at a right arm location on the patient, the second capacitive patient connector is connected at a left arm location on the patient, the third capacitive patient connector is connected at a left leg location on the patient, and the galvanic patient connector is connected at a right leg location on the patient.

3. The patient monitoring system of claim 1, wherein the physiological signals recorded include respiration potentials between the first capacitive patient connector and the second capacitive patient connector; and wherein the first capacitive patient connector and the second capacitive patient connector are drive electrodes to inject an AC current into the patient, and the galvanic patient connector acts as a ground.

4. The patient monitoring system of claim 1, wherein the first capacitive patient connector includes a first capacitive electrode and a first leadwire connecting the first capacitive electrode to the respective receiving port; and wherein the second capacitive patient connector includes a second capacitive electrode and a second leadwire connecting the second capacitive electrode to the respective receiving port.

5. The patient monitoring system of claim 1, wherein the first capacitive patient connector and the second capacitive patient connector each include a capacitive leadwire connectable to a galvanic electrode, the capacitive leadwire comprising:

an electrode end connectable to the galvanic electrode;
a first conductive layer extending from the electrode end;
a device end connectable to a data acquisition device;
a second conductive layer extending from the device end; and wherein the first conductive layer is galvanically isolated from the second conductive layer such that the first conductive layer and the second conductive layer form a capacitor.

6. The patient monitoring system of claim 5, wherein the first conductive layer and the second conductive layer are parallel wires divided by a substrate.

7. The patient monitoring system of claim 6, wherein the first conductive layer and the second conductive layer are comprised of a conductive ink printed on a substrate.

8. The patient monitoring system of claim 7, wherein the galvanic patient connector includes a conductive leadwire connectable to a galvanic electrode, wherein the conductive leadwire is comprised of a conductive ink printed on a substrate.

9. The patient monitoring system of claim 8, further comprising a resistor of at least 1 kilo-ohms printed on the conductive leadwire.

10. The patient monitoring system of claim 1, wherein the data acquisition device is a 12 lead electrocardiograph that records cardiac potentials from the patient, the 12 lead electrocardiograph having 10 receiving ports; and wherein the first receiving port connects to the galvanic patient connector, and the remaining nine receiving ports each connect to a respective capacitive patient connector.

11. A respiration monitoring system having defibrillation protection, the patient monitoring system comprising:

a data acquisition device that records cardiac potentials from a patient, the data acquisition device having at least three receiving ports, each receiving port configured to connect to a patient connector;

a galvanic patient connector that galvanically connects a first receiving port of the data acquisition device and the patient;

at least a first capacitive patient connector and a second capacitive patient connector, wherein each capacitive patient connector capacitively couples a respective receiving port of the data acquisition device and the patient;

wherein the cardiac potentials are recorded from the patient between the first capacitive patient connector and the second capacitive patient connector; and wherein the galvanic patient connector acts as a reference to remove a DC offset in the cardiac potentials.

12. The respiration monitoring system of claim 11, further comprising at least a third capacitive patient connector;

wherein the first capacitive patient connector is connected at a right arm location on the patient, the second capacitive patient connector is connected at a left arm location on the patient, the third capacitive patient connector is connected at a left leg location on the patient, and the galvanic patient connector is connected at a right leg location on the patient.

13. The respiration monitoring system of claim 12, wherein the galvanic patient connector is utilized to remove artifact caused by a change in a DC offset in the cardiac potentials recorded between the each of the capacitive patient connector, the second capacitive patient connector, and the third capacitive patient connector.

14. The respiration monitoring system of claim 11, wherein the first capacitive patient connector includes a first capacitive electrode and a first leadwire connecting the first capacitive electrode to the respective receiving port; and wherein the second capacitive patient connector includes a second capacitive electrode and a second leadwire connecting the second capacitive electrode to the respective receiving port.

15. The respiration monitoring system of claim 14, wherein the first capacitive patient connector and the second capacitive patient connector each include a capacitive leadwire connectable to a galvanic electrode, the capacitive leadwire comprising:

an electrode end connectable to the galvanic electrode;
a first conductive layer extending from the electrode end;
a device end connectable to a data acquisition device;
a second conductive layer extending from the device end toward the electrode end; and wherein the first conductive layer is galvanically isolated from the second conductive layer such that the first conductive layer and the second conductive layer form a capacitor.

16. The respiration monitoring system of claim 15, wherein the first conductive layer and the second conductive layer are parallel wires divided by a substrate.

17. A patient monitoring system having defibrillation protection, the patient monitoring system comprising:
- a data acquisition device that records physiological signals from a patient, the data acquisition device having at least three receiving ports, each receiving port configured to connect to a patient connector;
- a galvanic patient connector that galvanically connects a first receiving port of the data acquisition device and the patient; and
- at least a first capacitive patient connector and a second capacitive patient connector, wherein each capacitive patient connector capacitively couples a respective receiving port of the data acquisition device and the patient;
- wherein the physiological signals recorded include respiration potentials between the first capacitive patient connector and the second capacitive patient connector; and
- wherein the first capacitive patient connector and the second capacitive patient connector are drive electrodes to inject an AC current into the patient, and the galvanic patient connector acts as a ground.

* * * * *